(12) United States Patent
Brown

(10) Patent No.: US 10,660,629 B2
(45) Date of Patent: May 26, 2020

(54) APPARATUS FOR ILLUMINATING AN EYE

(71) Applicant: Mindskid Labs, LLC, Wilmington, NC (US)

(72) Inventor: Alan Wesley Brown, Wrightsville Beach, NC (US)

(73) Assignee: Mindskid Labs, LLC, Wilmington, NC (US)

( * ) Notice: Subject to any disclaimer, the term of this patent is extended or adjusted under 35 U.S.C. 154(b) by 0 days.

(21) Appl. No.: 15/940,078

(22) Filed: Mar. 29, 2018

(65) Prior Publication Data

US 2018/0280109 A1    Oct. 4, 2018

Related U.S. Application Data

(60) Provisional application No. 62/479,729, filed on Mar. 31, 2017.

(51) Int. Cl.
*A61B 17/02* (2006.01)

(52) U.S. Cl.
CPC ...... *A61B 17/0206* (2013.01); *A61B 17/0231* (2013.01)

(58) Field of Classification Search
CPC . A61B 17/02; A61B 17/0206; A61B 17/0218; A61B 17/0231
See application file for complete search history.

(56) References Cited

U.S. PATENT DOCUMENTS

| 5,556,417 | A | * | 9/1996 | Sher | A61B 17/0231 600/236 |
|---|---|---|---|---|---|
| 5,582,608 | A | * | 12/1996 | Brown | A61B 17/0231 606/4 |
| 5,695,492 | A | * | 12/1997 | Brown | A61B 90/20 606/4 |
| 8,311,624 | B2 | * | 11/2012 | Singh | A61B 17/0231 604/20 |
| 9,289,199 | B1 | * | 3/2016 | Sami | A61B 17/0231 |
| 9,610,072 | B2 | * | 4/2017 | Assia | A61B 17/0231 |
| 9,622,779 | B2 | * | 4/2017 | Horton | A61B 1/06 |
| 9,788,824 | B2 | * | 10/2017 | Assia | A61B 17/0231 |
| 9,999,345 | B2 | * | 6/2018 | Vayser | A61B 90/57 |
| 10,045,767 | B2 | * | 8/2018 | Assia | A61B 17/0231 |
| 10,285,680 | B2 | * | 5/2019 | Friedrich | A61B 17/0206 |

(Continued)

*Primary Examiner* — Eric S Gibson
(74) *Attorney, Agent, or Firm* — Douglas C. Tsao; F. Michael Sajovec; Williams Mullen

(57) ABSTRACT

The present invention provides an apparatus for illuminating the eye. This illumination may be by lamellar illumination, scleral scatter and retro illumination or a combination thereof. The apparatus comprises a speculum assembly and at least one light emitter assembly. The speculum assembly is adapted for magnetic attachment and includes a pair of flexible retractor arms extending from a speculum handle, each retractor arm including a retractor located distally from the speculum handle. The light emitter assembly is adapted for magnetic attachment and includes at least one flexible extension extending from a battery and circuit housing. The flexible extension includes a terminal optic emitter for adjusting the angle of inclination of light emitted therefrom. The speculum assembly and the light emitter assembly are magnetically mated together at one or more points of magnetic contact.

18 Claims, 5 Drawing Sheets

(56) References Cited

U.S. PATENT DOCUMENTS

| | | | |
|---|---|---|---|
| 2003/0109885 A1* | 6/2003 | Tano | A61F 2/1662 606/107 |
| 2003/0171656 A1* | 9/2003 | Foulkes | A61B 1/00094 600/232 |
| 2007/0060795 A1* | 3/2007 | Vayser | A61B 1/32 600/245 |
| 2010/0137780 A1* | 6/2010 | Singh | A61B 17/0231 604/20 |
| 2014/0323811 A1* | 10/2014 | DeSantis | A61B 1/06 600/213 |
| 2015/0065809 A1* | 3/2015 | Assia | A61B 17/0231 600/217 |
| 2015/0230787 A1* | 8/2015 | Friedrich | A61B 17/0206 600/213 |
| 2015/0359529 A1* | 12/2015 | Ganiban | A61B 17/0231 600/203 |
| 2016/0008088 A1* | 1/2016 | Vayser | A61B 90/57 600/178 |
| 2016/0192922 A1* | 7/2016 | Friedrich | A61B 90/30 600/214 |
| 2017/0202549 A1* | 7/2017 | Assia | A61B 17/0231 |
| 2017/0311801 A1* | 11/2017 | Benner | A61B 3/117 |
| 2018/0042597 A1* | 2/2018 | Assia | A61B 17/0231 |
| 2018/0280109 A1* | 10/2018 | Brown | A61B 90/30 |
| 2019/0008560 A1* | 1/2019 | Horton | A61B 1/06 |
| 2019/0083138 A1* | 3/2019 | Horton | A61B 1/06 |

\* cited by examiner

APPARATUS FOR ILLUMINATING AN EYE

RELATED APPLICATION

The present application relates to U.S. Provisional Application No. 62/479,729, filed Mar. 31, 2017, the disclosure of which is incorporated herein by reference in its entirety.

FIELD AND BACKGROUND OF THE INVENTION

The present invention relates generally to an apparatus for illuminating an eye undergoing eye surgery and, more specifically, to an apparatus for illuminating an eye, during surgery such as astigmatic keratotomy, cataract removal, LASIK, SMILE technique, corneal implant surgery, corneal transplant surgeries, glaucoma surgery pterygium surgery, retinal surgery and the like.

Conventionally, coaxially operating room microscope illumination is used to view the surgical field during eye surgery. Because of observed phototoxic effects of coaxial illumination, various filters or light-dimming techniques have been developed to reduce those effects. Still the operating room microscope places significant light coaxially into the patient's visual axis, which can result in retinal phototoxicity, patient discomfort and corneal drying.

Illumination approaching perpendicular directly over the pupil enters the eye directly through the pupil and stimulates the most sensitive back surface of the eye. This results in a patient sensation of extreme brightness, associated with discomfort and tearing.

Axial lighting requires high levels of illumination and the reflected light image creates glare from the projected light. The surgeon can experience difficulties during a procedure with glare that emanates from the axial light source reflecting from the anterior surface of the eye or associated structures and instrumentation back into the optics of the operating microscope and then into the surgeon's eyes.

The high intensity of axial light is often associated with a drying effect on the anterior structures of the eye secondary to a drying effect on the tear film. This drying can alter the thickness of the cornea and health of the surface tissue of the cornea (corneal epithelium), which in the setting of refractive surgery can result in serious surgical errors and complications. Further, phototoxicity of the posterior structures of the eye (retina) can occur with the use of strong axial microscope lighting and can cause permanent vision loss.

Thus, there is a continuing need for improved eye illumination apparatus which reduces light intensity, reduces drying effects to the eye decreases the light reaching the back of the eye to reduce patient discomfort and essentially eliminate phototoxicity, reduces glare and light reflected back into the microscope ocular, and provides improved visualization of the surgical field and instrument position.

SUMMARY OF THE INVENTION

The present invention provides an apparatus for illuminating the eye. This illumination may be by lamellar illumination, sclerotic scatter and retro illumination or a combination thereof. The apparatus comprises a speculum assembly and at least one light emitter assembly. The speculum assembly is adapted for magnetic attachment and includes a pair of flexible retractor arms extending from a speculum handle, each retractor arm including a retractor located distally from the speculum handle. The light emitter assembly is adapted for magnetic attachment and includes at least one flexible extension optionally extending from a battery and circuit housing. The flexible extension includes a terminal optic emitter for adjusting the angle of inclination of light emitted therefrom. The speculum assembly and the light emitter assembly are magnetically mated together at one or more points of magnetic contact.

BRIEF DESCRIPTION OF THE DRAWINGS

The present disclosure is illustrated and described herein with reference to the various drawings, in which like reference numbers denote like method steps and/or system components, respectively, and in which.

DETAILED DESCRIPTION OF THE INVENTION

The present approach may be understood more readily by reference to the following detailed description of various embodiments, taken in connection with the accompanying drawings, which form a part of this disclosure. It is to be understood that this disclosure is not limited to the specific embodiments, apparatus, devices, methods, or parameters described and/or shown herein, and that the terminology used herein is for the purpose of describing particular embodiments by way of example only, and is not intended to be limiting of the claims. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
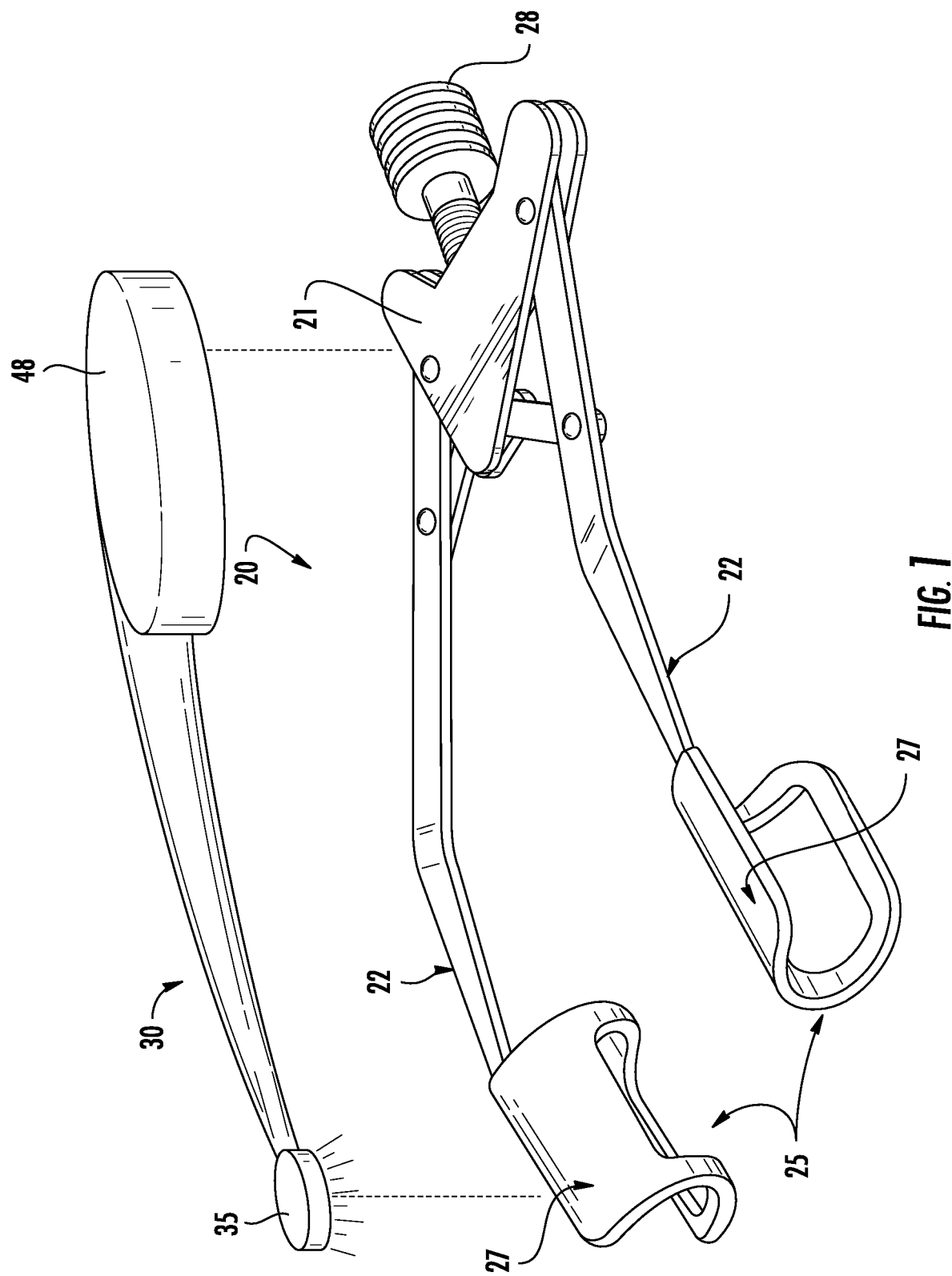
FIG. 1 is a perspective view of an embodiments of the present invention illustrating a magnetically single light emitter magnetically attached to a portion of the speculum.

Referring to FIG. 1, the apparatus for illuminating an eye of the present invention comprises a speculum assembly 20 and at least one light emitter assembly 30. In the present invention, the light emitter assembly 30 may direct light toward the surgical field. The light emitter assembly may include LEDs, fiber optics, laser emitting diodes, or other sources of light or radiation, magnets and the circuitry necessary for providing light or radiation. In one embodiment, the light emitter assembly 30 may be a light pipe such as described in PCT Application WO2015/164881 A1, the disclosure of which is incorporated by reference in its entirety. In some embodiments, a light emitter assembly emits light at an adjustable angle of from about 0 to about 90 degrees towards select portions of the cornea or sclera. In some embodiments, a light emitter assembly may be configured for emitting light at a desired angle or multi-angles, and/or on a desired location of or near the eye. Generally, select portions may include locations where light will not be reflected from the cornea surface back along the eye axis, and generally will not directly pass to the back of the eye. In some embodiments, light rays may be directed at the eye along paths as a slit-like or generally rectangular shape. The light emitter assembly may include means for polarizing or filtering the light.

The light emitter assembly 30 is configured to illuminate during eye surgery the interior of the eye by lamellar visible light and/or UV light above 235 nm or using infrared radiation up to about 910 nm. In some embodiments, the light may be directed as a slit beam, a ring-like or generally tubular volume, varying from a conical ring when the angle to the iris plan approaches zero to a tubular volume when the angle approaches 90 degrees of this ring. Such embodiments may provide illumination within which light is not conically focused through the pupil on to the central vision areas, the fovea, in the back of the eye.

When light is presented to the anterior surface of the eye (cornea) or at an acute angle, the cornea acts in the manner of a "light pipe," so that light entering at one edge of the cornea is internally reflected and passes in between and parallel to the anterior and posterior cornea surfaces, to exit 180 degrees away from the entrance illumination. Light may be diffused through the lamellae of the cornea for a distance from the light entrance. Light that projects onto the corneal scleral junction at an acute angle will thus be directed within the corneal lamellae which act as the light diffuser or light pipe. This light piping effect may be significantly enhanced by applying the optic (e.g., LED optic) directly onto the cornea to couple the light source to the cornea. Internal illumination of the eye can be achieved by coupling the optic to the sclera.

When light is presented to the anterior surface of the eye (cornea or sclera) in less acute angles or perpendicular to the iris plane, the light entering the eye is reflected off the iris or other eye structures and so retro illuminates the cornea and internal structures. Retro illumination provides a quality of light that enhances visibility of certain fine details and thus facilitates surgery.

Light directed perpendicular to the plane of the iris is by definition parallel to the pupillary/visual axis. However, light so directed will not enter the papillary axis if the parallel illumination is offset from the pupillary axis. The offset allows for the advantage of retro illumination of the cornea without the disadvantages of focused light coaxial to the pupillary axis. The offset is sufficient to prevent refraction of the offset light by the cornea into the pupillary axis.

Because the light is not directed perpendicularly through the central area of the pupil, very little light actually enters the eye to cause patient discomfort. Almost no light can enter the eye in a focused manner to reach the central posterior structure and cause photo toxicity to central vision. Similarly, there will be very little reflected light entering the microscope ocular. Instead, light refracted from the cornea projects to the microscope. Consequently, there is essentially no glare in the visualized structures and those visualized can be seen more clearly at lower light levels. This is particularly true when the surgery involves the cornea and involves altering the shape of the cornea through optical (laser) means or when corneal lamellar structures are incised in a procedure such as radial or astigmatic keratotomy or lamellar corneal surgery. In addition, because lower light levels can be used and light enters outside the visual axis or towards the edges of the cornea, the drying effect on the anterior surface of the eye is reduced.

Any of the embodiments of apparatus for introducing light in this manner at selected eye surface locations may be used, depending on the particular circumstances, such as, for example, the procedure to be performed and the need for illumination of specific tissue. Examples include lamellar illumination, scleral transillumination, sclerotic scatter, retro illumination or combinations thereof.

Generally lamellar lighting, which is a combination of scleral scatter and retro illumination, avoids significant light impact on the back of the eye and associated patient discomfort and phototoxicity. Lamellar lighting also typically avoids the glare which makes viewing a surgical field through a microscope difficult. Light may enter the eye at an angle of from about 0 degrees to about 90 degrees using embodiments of the apparatus hereinafter described. In particular circumstances, a particular angle within that range may be preferred. The iris is the contractile circular diaphragm forming the colored portion of the eye. Because generally lamellar lighting reveals any corneal discontinuity to scatter light in the absence of associated glare, and with a relatively dark background, these discontinuities glow brightly allowing excellent visualization. For example, in incisional refractive surgery, the incisions glow and the diamond knife intercepts the light and pipes it toward the diamond tip, making the exact location of the diamond tip easily visualized. These advantages are not possible with conventional microscope lighting. The plane of eye iris for the purposes of this application is considered to be the plane in which the outer edge of the iris substantially lies. Similarly, in femtosecond laser surgery of the cornea or crystalline lens, the discontinuities in cornea or lens created by the laser glow brightly with lamellar illumination in a manner not seen with conventional lighting.

Speculum assembly 20 may be constructed from, for example, a stainless steel with ferromagnetic properties to allow secure magnet attachment. The ferromagnetic properties may be localized to one or more portions or surfaces in some embodiments. An example would be Martensitic stainless steels. Non-ferromagnetic properties materials such as pyrolytic graphite, selenium, nickel or cobalt may also be used. The illustrated speculum assembly 20 includes a screw 28 to expand the retractor arms 22, but the principles can be applied to most speculum designs. Key areas that may require adequate magnetic adherence properties may include a landing pad 21 to fix the battery and circuit housing, an assembly on the retractor arms 22, which may be in some embodiments midway between the base 24 of the speculum assembly 20 and the retractor blades 25, and an area 27 on the retractor blades 25. It should be appreciated that the location, size, shape, and number of magnets and magnetic areas may vary depending on the particular embodiment, and the desired magnetic mating surfaces. Also, adhesive technologies and the like that are equivalent to magnet attachment may be used instead of magnetic attachment.

Magnetically attached to the speculum 20 and blade 25 is the single arm light emitter assembly 30. In this embodiment, light emitter assembly 30 mates with one of the speculum arms and blades of the speculum assembly 20 at magnetic mating surfaces landing blade 21, arms 22 and/or blades 27. The advantage of the single arm light emitter assembly 30 embodiment is the ability to direct light using the inferior retractor blade, thus leaving the upper blade clear of any obstruction that may interfere with surgical instruments. Although the image shows a flexible enclosure with magnet attachment on the terminal optic 35, embodiments may be made of firm material, and may contain at least one additional magnet over the battery section 48 of the light emitter assembly 30. The terminal optic 35 and the battery section 48 may be tethered together with a flexible electrical wire. The magnets can also be configured to become part of the activation circuit using the metal of the speculum assembly 20 to complete the electrical pathway of the light emitter assembly 30. In lieu of individually placed magnets, the entire flexible covering of the light emitter assembly 30 could be infused with magnetic particles (e.g., powdered ferrite) in a liquid binding agent and applied to the light emitter assembly 30.

Figure 2:
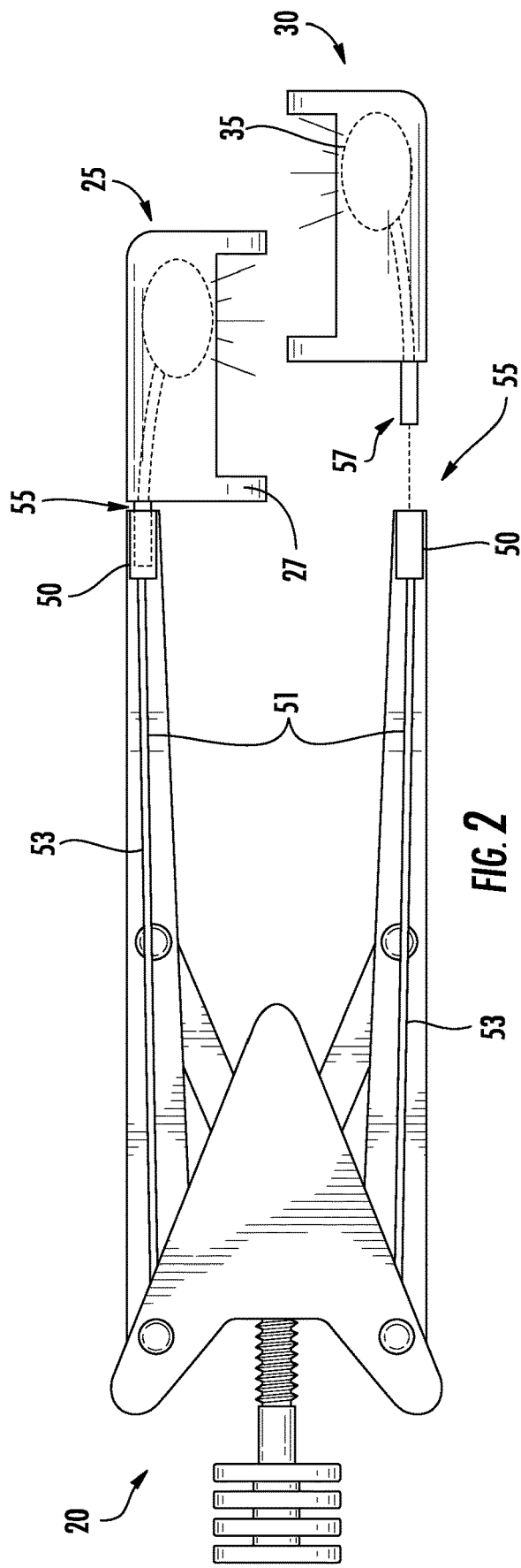
FIG. 2 is an embodiment of the present invention illustrating removal retractor blades.

FIG. 2 shows an embodiment of the invention including of a speculum assembly 20 (light emitter assembly not shown) with terminal receptacles 50 that contain one magnet in contact with an electrical wire 51 and a separate contact that connects to a wire 53 of an opposite charge. The light emitter assembly 30 that mates into socket 55 has a male segment with terminal contact 57 that, when mated with socket 55 completes half of the circuit to the terminal optic 35 positioned in the blades 25 of the light emitter assembly 30. The second contact proximal to the area 27 of the retractor blade 25 similarly mates to the other socket 55. The circuit is then completed (not shown). If needed, an o-ring may be provided at the entrance to a socket in order to protect the socket environment from liquid splash during surgery.

Figure 3:
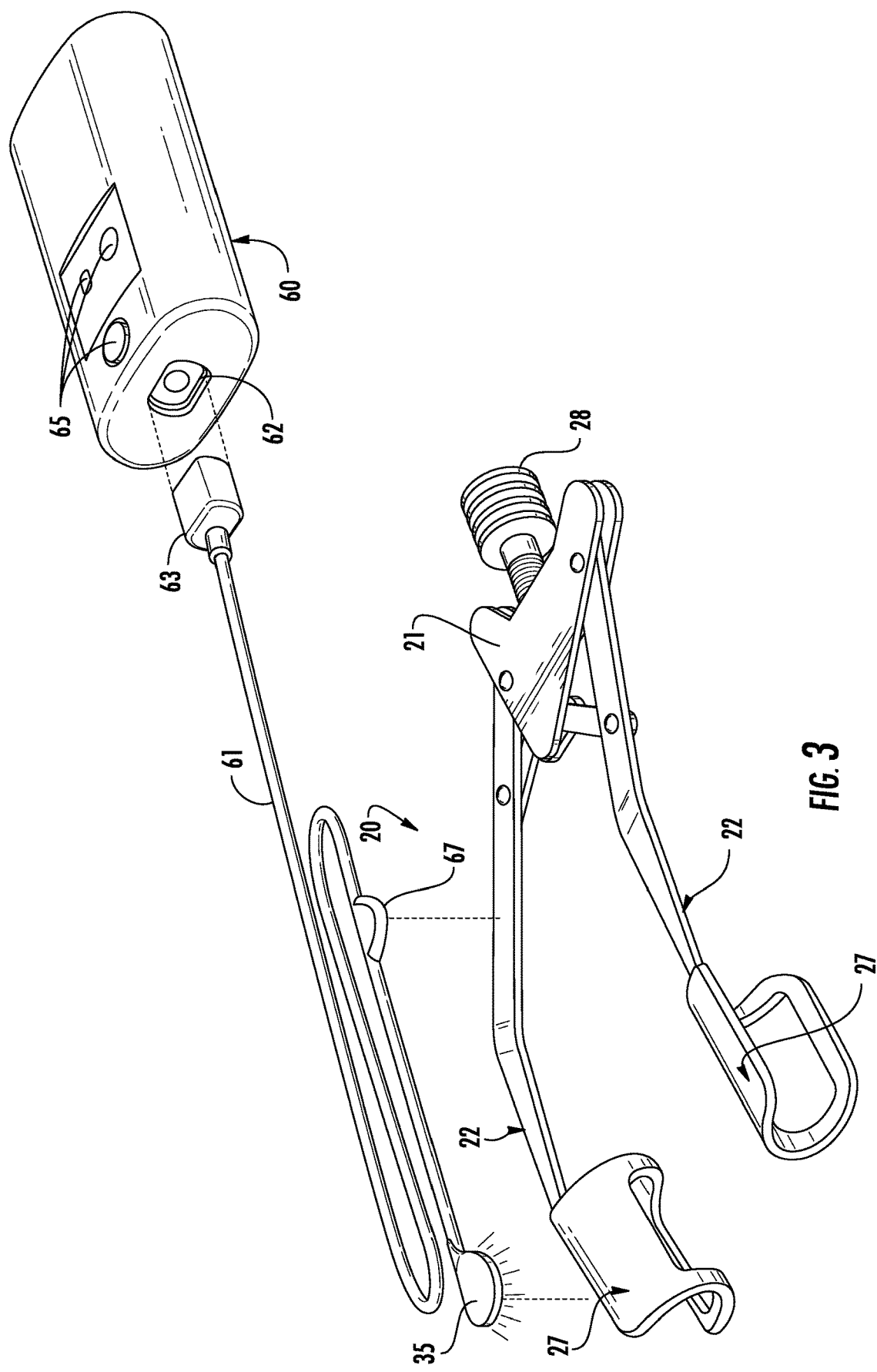
FIG. 3 is a perspective view of an embodiment of the present invention illustrating an alternative magnetically single light emitter magnetically attached to a portion of the speculum.

FIG. 3 illustrates an alternative embodiment in which a power source 60 is separate from the power wire 61. The tethered power wire during use may be plugged into socket 62 via a magnetic plug 63. The power source 60 may supply direct power and be connected during use or may charge the terminal optic 35. The power source may require an authentication code for use. The power wire 61 with the terminal optic may be adapted so as to be disposable, i.e., as a "one use" assembly. In such case, the authentication code may be programmed so that the one-use assembly cannot be used multiple times. The power source may include indicia 65 (e.g., using LEDs) indicating, for example, whether the power source 60 and power wire are connected or that the terminal optic 35 is in a charged condition or how much time or life is left on the battery. The power wire 61 may include a metal hook 67 or clasp to facilitate magnetic attachment of the power wire 67 to the arms 22.

Figure 4:
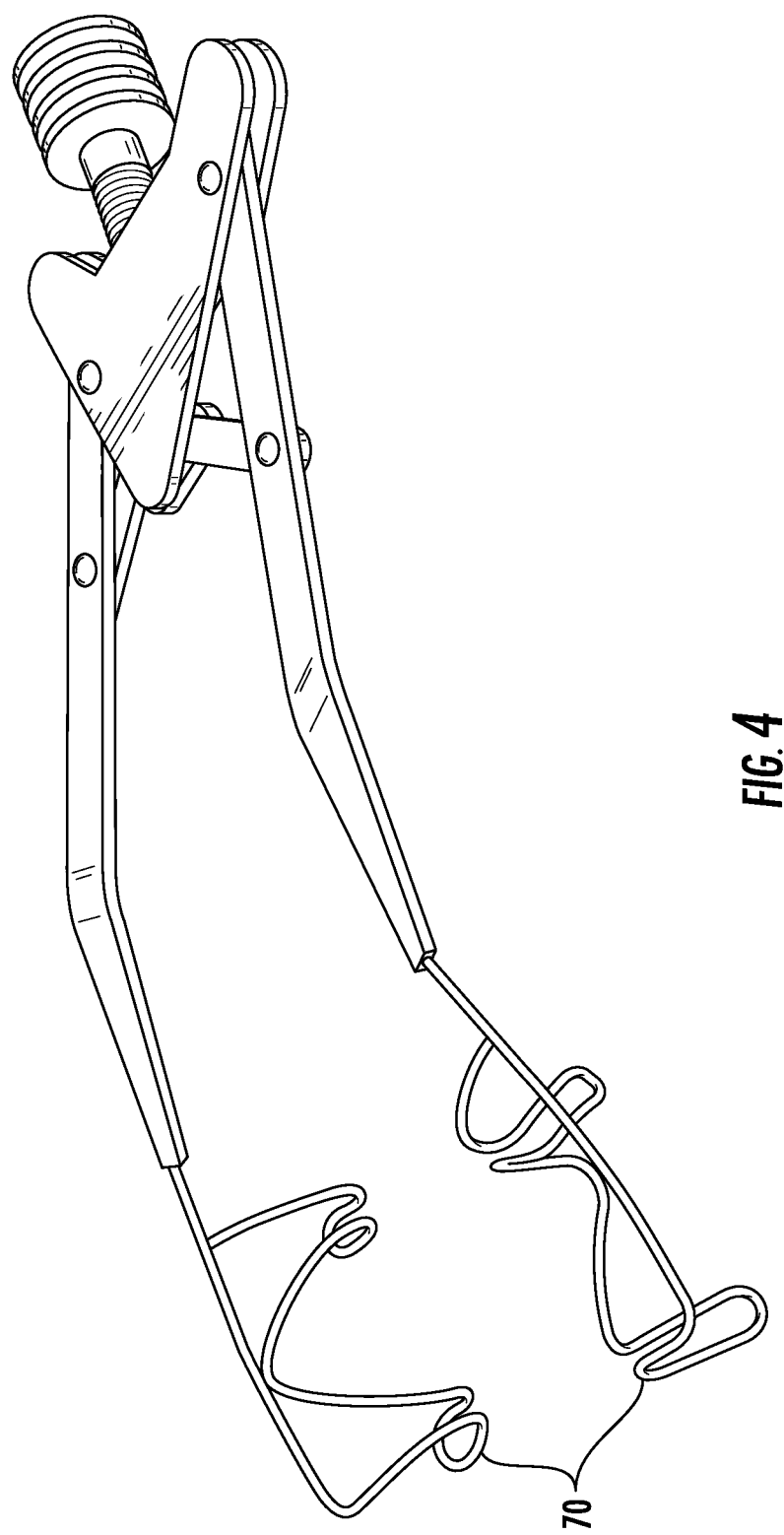
FIG. 4 is an embodiment of the present invention illustrating an alternative embodiment of the speculum with a wire structure replacing the speculum retractor blades.

FIG. 4 illustrates an alternative embodiment of the speculum assembly 20 having wire blades 70 instead of the closed blades shown and described previously. The wire blades 70 in combination with a variety of placements of magnets on the terminal optics (not shown) may have a wide variety of geometries to allow the terminal optic to be positioned to emit light at multiple angles.

Figure 5:
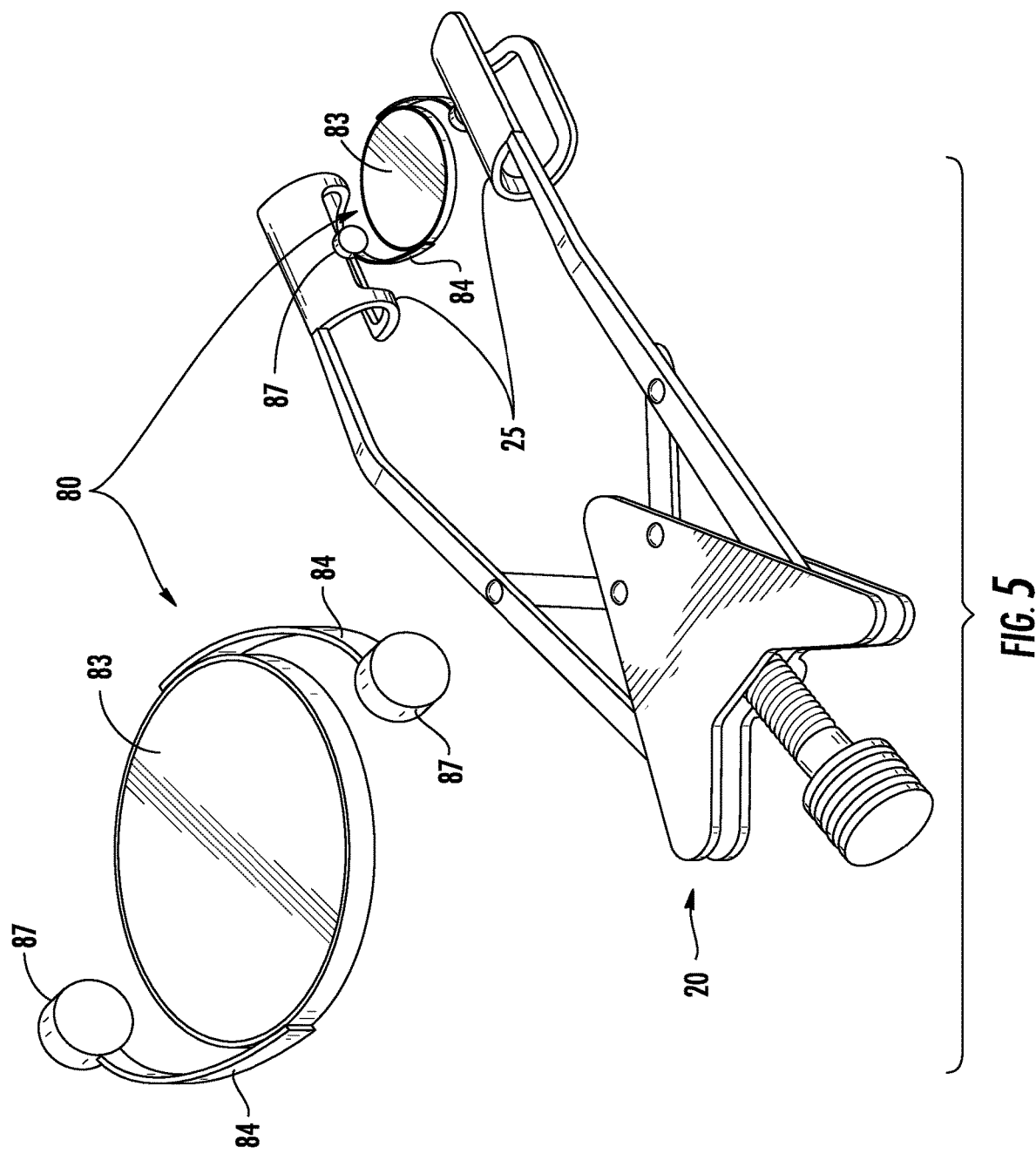
FIG. 5 is an embodiment of the present invention illustrating a magnetic bridge attached to the speculum assembly.

FIG. 5 shows an embodiment of a magnetic connecting bridge assembly 80 that can be attached to the speculum assembly 20 to increase surface area for magnetic mating surfaces for placement of one or more optic/LED emitters. For example, a lens 83 may be placed in arms 84 and the assembly 80 attached to the blades 25 using magnets 87. This embodiment may be advantageous for certain surgical cases such as for glaucoma or retinal surgery in which light may be needed outside the confines of the magnetic zone of the retractor.

Although the present approach has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present approach.

That which is claimed is:

1. A speculum apparatus for illuminating an eye, the apparatus comprising:
   a speculum assembly adapted for magnetic attachment and comprising a pair of flexible retractor arms extending from a speculum handle, each retractor arm including a retractor located distally from the speculum handle, and
   a light emitter assembly adapted for magnetic attachment and comprising at least one flexible extension extending from a battery and circuit housing, said flexible extension including a terminal optic emitter for adjusting an angle of inclination of light emitted therefrom, wherein the speculum assembly and light emitter assembly are magnetically mated together at one or more points of magnetic contact.

2. The apparatus of claim 1, wherein the light emitter assembly is configured to illuminate during eye surgery the eye by lamellar visible light and/or UV light above 235 nm or by infrared radiation up to 910 nm.

3. The apparatus of claim 1, wherein the light is directed in a slit beam, ring-like or tubular volume.

4. The apparatus of claim 1, wherein the light emitter assembly is configured to emit light that enters the eye at an adjustable angle of from 0 to 90 degrees.

5. The apparatus of claim 1, wherein the eye is illuminated by lamellar illumination, sclera transillumination, sclerotic scatter, retro illumination, or a combination thereof.

6. The apparatus of claim 1, wherein the light emitter assembly is configured illuminate an eye by coupling the optic of the terminal optical emitter to a sclera of the eye.

7. The apparatus of claim 1, wherein the speculum assembly is constructed from a stainless steel with ferromagnetic properties.

8. The apparatus of claim 1, wherein the magnetic attachment is provided by nickel, cobalt, selenium, or pyrolytic graphite.

9. The apparatus of claim 1, wherein the terminal optic emitter comprises LED, fiber optic, and/or laser emitting diodes emitters.

10. The apparatus of claim 1, further comprising a connecting bridge assembly magnetically mated to the pair of flexible retractor arms.

11. The apparatus of claim 10, wherein the connecting bridge assembly comprises arms and a lens placed in the arms.

12. The apparatus of claim 1, wherein the flexible extension extending from the battery is a tethered power wire, wherein the power wire can be separated from the battery.

13. A speculum apparatus for illuminating an eye, the apparatus comprising:
   a speculum assembly adapted for magnetic attachment and comprising a pair of flexible retractor arms extending from a speculum handle, each retractor arm including a retractor located distally from the speculum handle, and
   a single arm light emitter assembly adapted for magnetic attachment to the pair of flexible retractor arms, the single arm light emitter assembly comprising a flexible extension including a terminal optic emitter for adjusting an angle of inclination of light emitted therefrom, wherein the speculum assembly and the single arm light emitter assembly are magnetically mated together at one or more points of magnetic contact.

14. The apparatus of claim 13, wherein the speculum assembly and single arm light emitter assembly are magnetically mated together by individually placed magnets.

15. The apparatus of claim 13, wherein the speculum assembly and single arm light emitter assembly are magnetically mated together through application of magnetic particles onto a surface of the speculum assembly and magnetic particles embedded into or coated onto a surface of the single arm light emitter assembly.

16. The apparatus of claim 13, further comprising a connecting bridge assembly magnetically mated to the pair of flexible retractor arms.

17. The apparatus of claim 16, wherein the connecting bridge assembly comprises arms and a lens placed in the arms.

18. The apparatus of claim 13, wherein the flexible extension extending from a battery is a tethered power wire, wherein the power wire can be separated from the battery.

* * * * *